United States Patent [19]
Law

[11] Patent Number: 6,103,702
[45] Date of Patent: Aug. 15, 2000

[54] USE OF ADENOSINE DEAMINASE INHIBITORS TO TREAT SYSTEMIC INFLAMMATORY RESPONSE SYNDROME

[75] Inventor: William R. Law, Brookfield, Ill.

[73] Assignee: Board of Trustees of the University of Illinois, Urbana, Ill.

[21] Appl. No.: 09/317,678

[22] Filed: May 24, 1999

[51] Int. Cl.[7] ..................................................... A61K 31/70
[52] U.S. Cl. ................................................. 514/46; 514/45
[58] Field of Search ......................................... 514/46, 45

[56] References Cited

U.S. PATENT DOCUMENTS 5,703,084  12/1997  Abushanab et al. ..................... 514/261
5,731,432   3/1998  Erion et al. .............................. 540/554

FOREIGN PATENT DOCUMENTS 9823267  11/1997  WIPO .

Primary Examiner—Theodore J. Criares
Assistant Examiner—Jennifer Kim
Attorney, Agent, or Firm—Barnes & Thornburg; Alice O. Martin

[57] ABSTRACT

Methods of treating various-inflammatory conditions, including systemic inflammatory response syndrome (SIRS), septic shock and burns, conditions which may be ameliorated by increased local concentrations of adenosine using adenosine deaminase inhibitors are provided.

11 Claims, 7 Drawing Sheets

SERUM TUMOR NECROSIS FACTOR--ALPHA

USE OF ADENOSINE DEAMINASE INHIBITORS TO TREAT SYSTEMIC INFLAMMATORY RESPONSE SYNDROME

This invention relates to a new use of adenosine deaminase inhibitors in the treatment of inflammation, sepsis, septic shock, burns and diseases. These conditions are ameliorated by increasing the local concentration of adenosine in affected regions.

BACKGROUND OF THE INVENTION

Conditions resulting in or from a systemic inflammatory response syndrome (SIRS) are associated with an exaggerated immune response, oxygen free-radical-mediated injury, and tissue perfusion maldistribution. Such conditions include endotoxin shock, septic shock, sepsis, endotoxemia, septicemia, peritonitis, and adult respiratory distress syndrome (ARDS). Current treatment is unsatisfactory. Therapeutic attempts to modify cytokine responses during SIRS-related conditions have focussed on antibodies to the cytokines or cytokine receptor antagonists. These approaches have proven unsuccessful because some level of cytokine response is required for survival from SIRS-related conditions.

Adenosine has been reported to be an endogenous modulator of inflammation by virtue of its effects on stimulated granulocyte function (Cronstein et al., 1986) and on macrophage, lymphocyte and platelet function. Adenosine receptor agonists have been reported to be beneficial in an experimental model of inflammation (Schrier et al., 1990). Adenosine and a related analog have been reported to inhibit in vitro production of the cytokine, tumor necrosis factor alpha (Parmely et al., 1991). Antibodies to TNF-α have not been shown to alter mortality in sepsis (Abraham et al. 1998, Cohen et al. 1996, Amiot et al. 1997).

Adenosine is an endogenous, ubiquitous molecule that modulates immune function, can suppress or increase free-radical production, and produces vasodilation in regions wherein adenosine is produced in significant quantities.

Adenosine has a short half life (<1 sec) in human blood (Moser et al., 1989), and therefore high doses of adenosine would need to be administered continuously to achieve effective treatment levels. Adenosine has been reported to exhibit negative inotropic, chronotropic and dromotropic effects (Belardinelli et al., 1989) and to cause coronary steal by preferentially dilating vessels in nonischemic regions. Consequently, high doses of adenosine are toxic and this toxicity severely limits its therapeutic potential. However, by increasing adenosine concentration locally, i.e. at the target site within the target tissue, the beneficial effects of adenosine might be provided without the toxic systemic effects.

Riches et al. (1985) reported that adenosine inhibited β-galactosidase secretion from zymosan particle-stimulated mouse peritoneal macrophages. The adenosine nucleotides ATP, ADP, and AMP were also effective inhibitors, but only after hydrolysis to adenosine. These authors found that the inhibitory effect of adenosine in vitro could be increased with erythro-9-(2-hydroxy-3-nonyl) adenine (EHNA), a potent inhibitor of adenosine deaminase. By thus inhibiting adenosine breakdown to inosine and hypoxanthine the inhibitory effects of adenosine were prolonged. Similarly, Itoh et al. (1989) reported that both adenosine and 1-methyladenosine inhibited chemiluminescence by zymosan-stimulated mouse peritoneal macrophages in vitro.

Adenosine has been shown to inhibit TNF-α produced in response to endotoxin (LPS). Using LPS, Eigler et al. stimulated isolated human peripheral blood mononuclear cell production of TNF-α. The addition of adenosine deaminase (increasing endogenous adenosine degradation) or an adenosine $A_2$ receptor antagonist further increased TNF-α production, while an adenosine $A_1$ receptor antagonist had no effect. This indicated that endogenous adenosine production after stimulation with LPS served to limit the TNF-α response of the monocyte. Eigler et al. further demonstrated that TNF-α production by LPS-stimulated monocytes could be inhibited by dipyridamole, an agent that prevents cellular adenosine reuptake a major pathway for adenosine removal by monocytes (Barankiewicz, 1989). Adenosine-modulated TNF-α production by other cell types has also been shown. Cronstein et al. examined leukocyte accumulation and TNF-α production in skin air pouches injected with carrageenan. Endogenous adenosine concentrations were altered by inhibiting adenosine kinase, an enzyme contributing to nucleotide salvage via phosphorylation of adenosine. Pretreatment of rats with oral GP1-515, an adenosine kinase inhibitor (reducing adenosine salvage into nucleotides), reduced leukocyte accumulation and TNF-α production. TNF-α concentration in the pouch exudates were reduced from 1518 pg/ml to 780 pg/ml. The direct involvement of adenosine in this response was proven by reversing the inhibitory effects of GP-1-515 with either excess exogenous adenosine deaminase or an adenosine $A_2$ receptor antagonist.

An adenosine kinase inhibitor, GP-1-515, produced by Gensia Inc., is reported to elevate local adenosine concentrations in tissues. Adenosine deaminase is a cytosolic and membrane-bound enzyme which catalyzes the deamination of adenosine to inosine, a necessary step prior to entry of adenosine catabolites into the xanthine oxidase pathway to form uric acid. Inhibition of adenosine deaminase can reduce the rate at which extracellular adenosine is degraded, leading to increased adenosine outside of the cell where it is pharmacologically active. Inhibition of ADA has such an effect. In isolated guinea pig hearts addition of the adenosine deaminase inhibitor, EHNA, to the perfusion medium, in the presence of 5'-amino-5'-deoxyadenosine to inhibit phosphorylation of adenosine to AMP, was reported to result in a 15-fold increase of adenosine release (Schrader, 1983). These effects were not apparent in the absence of ADA inhibition.

In an effort to find effective treatments for SIRS and related conditions, inhibitors of adenosine deaminase were explored.

SUMMARY OF THE INVENTION

The present invention is directed to novel uses of compounds which are potent and selective adenosine deaminase inhibitors. Another aspect of the present invention is directed to the clinical use of adenosine deaminase inhibitors as a method of increasing adenosine concentrations in biological systems. To treat a mammal in need thereof, an effective amount of an adenosine deaminase inhibitor is administered to the person. An "effective amount" is that dose which will ameliorate symptoms in the mammal to whom it is administered. In vivo inhibition of adenosine deaminase prevents deamination of adenosine resulting in higher local concentrations of endogenous adenosine than present before treatment. As a result of the very short half-life of adenosine and very low quantities of adenosine in tissues, this effect is most pronounced in regions producing the most adenosine such as ischemic regions or regions undergoing elevated adenylate cyclase activity. Hence, the beneficial effects of adenosine are enhanced in site and event specific manners and toxic systemic effects are reduced.

Adenosine deaminase inhibitors may be used clinically to treat medical conditions where an increased localized adenosine concentration is beneficial. Accordingly, the present invention is directed to the prophylactic and affirmative treatment of conditions benefited by enhanced adenosine levels such as inflammation, arthritis, autoimmune diseases, cardiac arrhythmias, ulcers and irritable bowel syndrome. In particular, the present invention is also directed to the prophylactic and affirmative treatment of sepsis, septicemia (including endotoxemia), and various forms of septic shock (including endotoxic shock.) For example, adenosine deaminase inhibitors are useful in the prophylactic or affirmative treatment of a localized or systemic inflammatory response to infection by one or more of several types of organisms, including bacteria (gram negative or gram positive), viruses (including retroviruses), mycobacteria, yeast, protozoa or parasites. Furthermore, the present invention is directed to the treatment of disorders in which vascular leakage is involved. In particular, the present invention is directed to the treatment of burn injury.

Methods of treating systemic inflammatory response syndrome (SIRS) include administering an inhibitor of adenosine deaminase, which results in increased local concentrations of adenosine in tissues. There are no other therapeutic agents that are used in the art for the treatment of SIRS which act via inhibition of adenosine deaminase. The use of an adenosine kinase inhibitor (Firestein et al., 1994) has the deleterious potential to reduce cellular nucleotide stores, and increase oxyradical-mediated damage via the degradation of the resultant increased endogenous adenosine. In contrast, an adenosine deaminase inhibitor increases local adenosine concentrations, while simultaneously preventing adenosine's entry into the xanthine oxidase pathway. Neither does it interfere with the re-phosphorylation of adenosine into cellular nucleotides. As such, the treatment of sepsis and SIRS by inhibiting adenosine deaminase amplifies regional vasodilatory and immuno-modulating effects of adenosine, but is superior to adenosine kinase inhibition by reducing oxygen free radical-mediated damage that occurs via the xanthine oxidase pathway, and increases the amount of adenosine available for high energy nucleotide repletion. Two advantages of inhibition of adenosine deaminase over inhibition of adenosine kinase to treat SIRS are as follows:

1. inhibition of adenosine deaminase reduces oxyradical-mediated tissue damage that occurs via adenosine breakdown through the xanthine oxidase pathway; and
2. inhibition of adenosine deaminase will not prevent maintenance of cellular high energy adenine nucleotides that occurs via adenosine kinase.

Therapeutic approaches of the present invention to combat the relevant physiological systems in SIRS by inhibition of adenosine deaminase are singularly targeted. Thus, the use of inhibitors of adenosine deaminase circumvent the need for multiple therapeutic approaches. This simplifies the treatment of SIRS, and is likely to be more cost effective.

The method of the present invention increases adenosine concentrations only in regions wherein it is produced. The regions wherein adenosine is produced during sepsis are the hepatosplanchnic and skeletal muscle regions. The method is superior to the use of adenosine analogues in that adenosine analogues exert systemic effects, having potential to cause refractory hypotension, inappropriate bradycardia, and myocardial depression. An advantage of the method of the present invention is that cytokine responses are merely modulated, rather than abated.

Administration of an adenosine deaminase inhibitor such as pentostatin increases local endogenous adenosine concentrations. This leads to several important effects: amplification of anti-inflammatory cytokines, such as IL-10, and suppression of pro-inflammatory cytokines, such as TNF-$\alpha$. Increasing endogenous adenosine by this method increases tissue perfusion in the locale wherein adenosine production is increased. Increased endogenous adenosine by this method inhibits neutrophil accumulation, adhesion, and activation leading to oxygen free-radical-mediated damage of tissue in the locale wherein adenosine production is increased. Inhibition of adenosine deaminase also reduces the amount of oxygen free-radical-mediated damage by reducing substrate flow through the xanthine oxidase metabolic pathway.

Inhibitors suitable for practice of the invention include pentostatin, EHNA, ARADS.

DETAILED DESCRIPTION OF THE INVENTION

Conditions resulting with or from inflammatory response syndrome (SIRS) are associated with an exaggerated immune response, oxygen free radical-mediated injury, and tissue perfusion maldistribution. Adenosine is a ubiquitous molecule that modulates immune function, can suppress or increase free-radical production, and produces localized vasodilation. In vitro, adenosine is capable of suppressing macrophage activation and limiting cytokine release. Adenosine also attenuates neutrophil adherence and production of reactive oxygen radical moieties by neutrophils.

Adenosine becomes an important vasoactive mediator in sepsis. The majority of the evidence regarding adenosine's immuno-modulating role comes from in vitro studies. These cannot be easily extrapolated to the in vivo immune response associated with sepsis. Thus, the claim that the ability to amplify endogenous adenosine's capabilities to perform these functions in vivo during sepsis by inhibiting adenosine deaminase comes from experiments disclosed herein. One of the advantages of altering adenosine concentrations in vivo by manipulating the adenosine metabolic pathways is that it would only affect regions wherein endogenous adenosine is being produced in significant quantities, and would have no effect in other regions.

Figure 1:
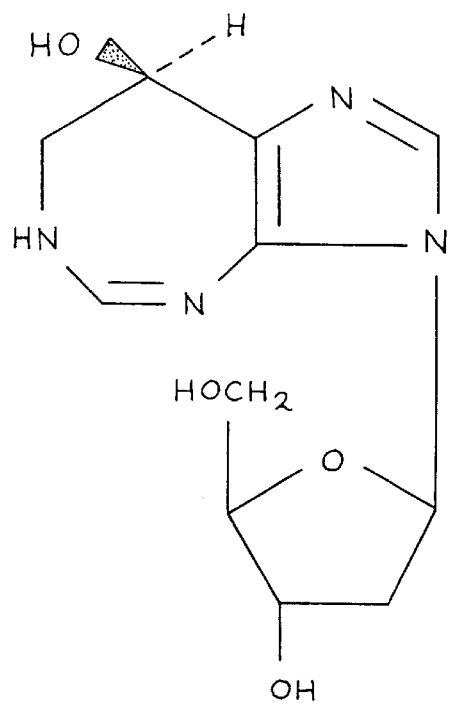
FIG. 1 shows the chemical structure of pentostatin where O=oxygen, H=hydrogen, N=nitrogen, C=carbon, and the bonding is shown as standard in the art.

Adenosine concentrations are increased locally by treatment with adenosine deaminase inhibitors such as pentostatin. Pentostatin is (R)-3-(2-deoxy-beta-Derythropentofuranosyl)-3,6,7,8-tetrahydro-imidazo[4,5-d]-[1,3]diazepin-8-ol having the structure shown in FIG. 1. It is a potent adenosine deaminase inhibitor and is useful as an antileukemic agent. U.S. Pat. No. 3,923,785, issued Dec. 2, 1975, describes the production of pentostatin by fermentation of a strain of Streptomyces antibioticus which is on deposit as NRRL 3238. U.S. Pat. No. 3,923,785 also describes the isolation and purification of pentostatin from the fermentation of beer.

Adenosine as an Important Vasoactive Mediator in Sepsis

Adenosine is recognized as a potent vasodilator that serves as a regional regulator of tissue perfusion. Endogenous adenosine is an important mediator of reduced resting vascular tone during sepsis to maintain elevated perfusion of selected tissues. A benefit of increasing endogenous adenosine concentrations by inhibiting adenosine deaminase is to increase perfusion in affected tissues wherein endogenous adenosine evolution is increased.

Despite its proximal importance in the inflammatory response to infection, TNF-α concentrations are not an optimal index of mortality in septic patients. In contrast, IL-6, which is stimulated by TNF-α, is a more sensitive index of the inflammatory response to sepsis, and correlates with mortality (Adamik et al., 1997; Meduri et al., 1995; Meduri et al.; Chest; 107,1062–1073). In addition, the anti-inflammatory cytokine IL-10 may play an important role, and it has been suggested that the best indicator of impending multiple organ failure and mortality may be an understanding of the balance of these cytokines (Walley 1996; Casey et al., 1993; Koto, et al., 1995). Relevant to this proposed used of adenosine deaminase inhibition, IL-10 and IL-6 are also modulated by adenosine in vitro (LeMoine et al. 1996; Hosko et al., 1996; and Ritchie, et al., 1997).

Endogenous Adenosine Modulates Oxyradical Damage During Sepsis

Three pathways have been demonstrated to be involved in oxygen free radical production during sepsis: the arachidonic acid pathway (via cyclo-oxygenase), neutrophil activation and degranulation, and from adenosine catabolites via xanthine oxidase (Schiller et al. 1993). Allopurinol, a specific inhibitor of xanthine oxidase, protects the bowel from hypoperfusion and increased intestinal permeability caused by endotoxin, indicating a significant role for xanthine oxidase-mediated damage (Xu et al., 1993; Castillo et al., 1991) demonstrated significantly better survival using allopurinol in their rodent model of cecal ligation and puncture. In addition, rat hepatic sequestered neutrophils produce superoxides after in vivo endotoxin infusion (Spitzer et al., 1994). These studies suggest that oxygen free radical-mediated hepato-splanchnic damage occurs after a septic challenge, and that both neutrophil and xanthine oxidase pathways of production are involved.

Adenosine has also been shown to inhibit a variety of neutrophil functions, including adherence, TNF-stimulated lactoferrin secretion and $H_2O_2$ production. Both adenosine, and the adenosine A2 receptor agonist, NECA, inhibit neutrophil adherence and H2O2 production, while N6-phenylisopropyladenosine, and A1 receptor agonist, actually promote neutrophil adherence.

Oxygen free radical injury, characteristic of sepsis, could also be a result of adenosine accumulation. The fate of adenosine that enters the xanthine oxidase pathway has been explored extensively in the heart. While adenosine can be active as a vasodilator under conditions of hypoperfusion, its half-life is extremely short, as it is rapidly taken up by other cells, particular vascular endothelium (Becker et al. 1987). During constant perfusion of rat hearts with a hypoxic solution, Becker and Gerlach demonstrated elevations in coronary venous effluent uric acid, accounting for up to 73% of the total amount of purine in the venous effluent. Allopurinol (10nM) reduced uric acid production to below detectable levels, confirming that the source of the uric acid was the xanthine oxidase pathway. While hypoxanthine levels increased modestly, there was little other evidence of substrate backup, and radiotracer experiments showed reduction in cellular purine release. Thus, it appears that under hypoxic perfused conditions, adenosine can provide substantial substrate through the xanthine oxidase pathway. In a model of coronary ischemia and reperfusion inhibition of adenosine deaminase with erythro-9-(2-hydroxy-3-nonyl)adenine (EHNA) significantly reduces the amount of adenosine capable of entering the xanthine oxidase pathway, resulting in improved functional recovery from ischemia, reduction of the concentrations of adenosine catabolites, and greater increases in tissue ATP concentrations after reperfusion, an important consideration when increasing endogenous adenosine levels using an adenosine deaminase inhibitor. This treatment method blocks the entry of adenosine into the xanthine oxidase pathway, but allows endogenous adenosine to re-enter the cell for rephosphorylation by adenosine kinase. In contrast, inhibition of adenosine kinase can be used to increase interstitial adenosine concentrations, but this approach allows the increased endogenous adenosine to enter the xanthine oxidase pathway (resulting in increased oxygen free radicals by this pathway) and prevents adenosine from being used in nucleotide salvage. Inhibition of adenosine deaminase is effective in reducing oxygen free radical-mediated damage during sepsis. This mode of elevating endogenous adenosine should be particularly effective in sepsis, wherein both localized oxygen supply-dependent perfusion imbalances and neutrophil activation can be deleterious.

Figure 2:
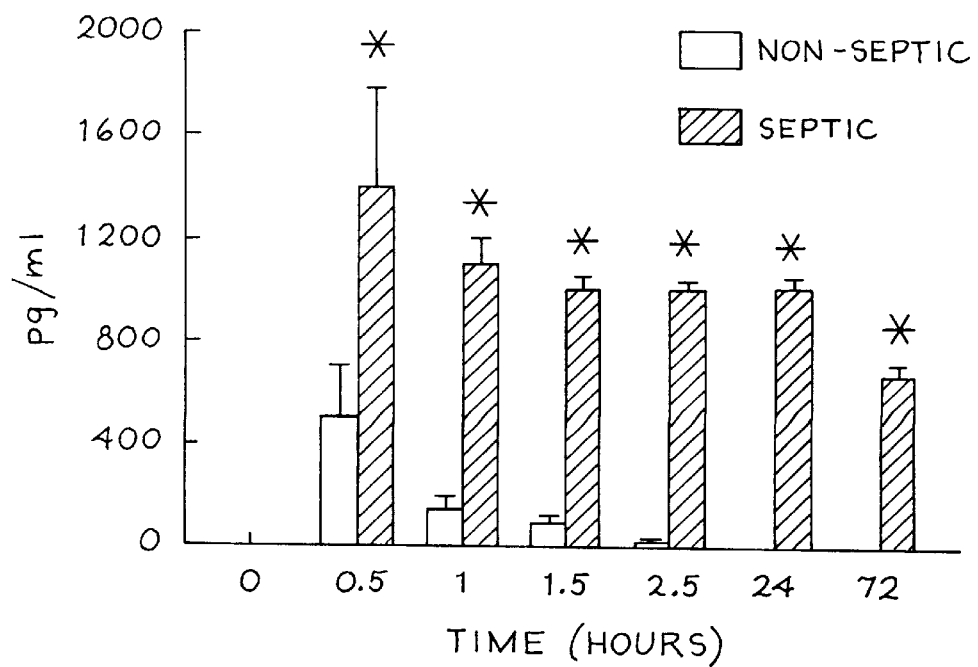
FIG. 2 graphically presents the relation between serum tumor necrosis factor-alpha and sepsis over time.
Figure 3:
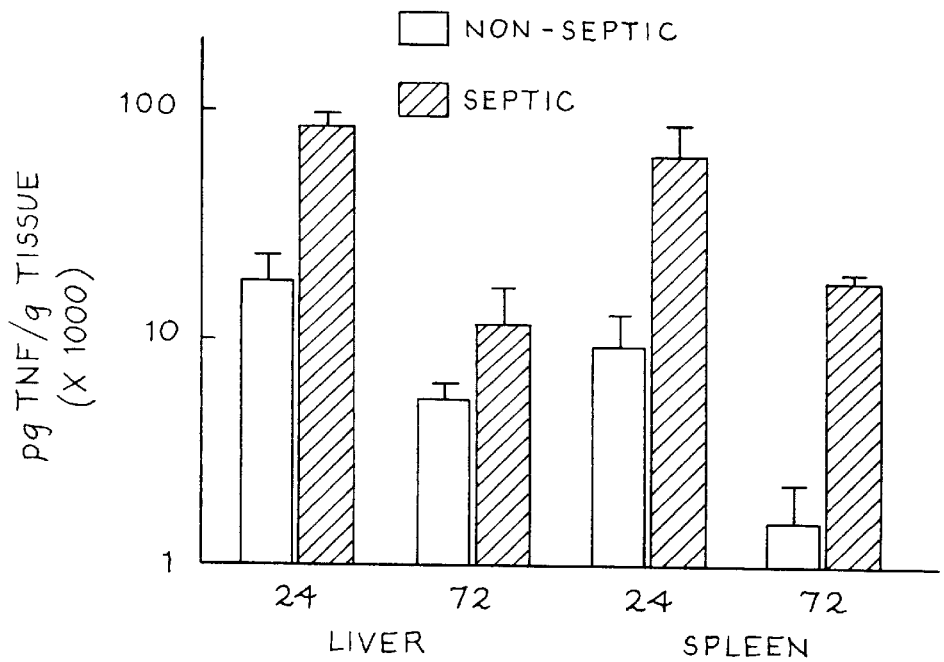
FIG. 3 graphically depicts the level of TNF in liver and in spleen over time in septic and non-septic animals.

The model of sepsis used is associated with elevated serum concentrations of TNF-α as early as 30 minutes after sepsis induction, and these concentrations remain elevated up to 72 hours (FIG. 2). TNF-α was also elevated at 24 and 72 hours in samples of liver and spleen in septic rats (FIG. 3). The surgical procedure (non-septic controls) used to induce sepsis also resulted in elevation of TNF-α in these tissues at 24 hours, but these were significantly lower than in the septic rats. The animals clearly demonstrate other indicators of progressive sepsis (progressive leukocytosis, lactacidemia) through day 7. These data demonstrate that 24–72 hours of sepsis in our model is an appropriate time frame in which to examine the ability of adenosine to modulate TNF-α in vivo.

Figure 4:
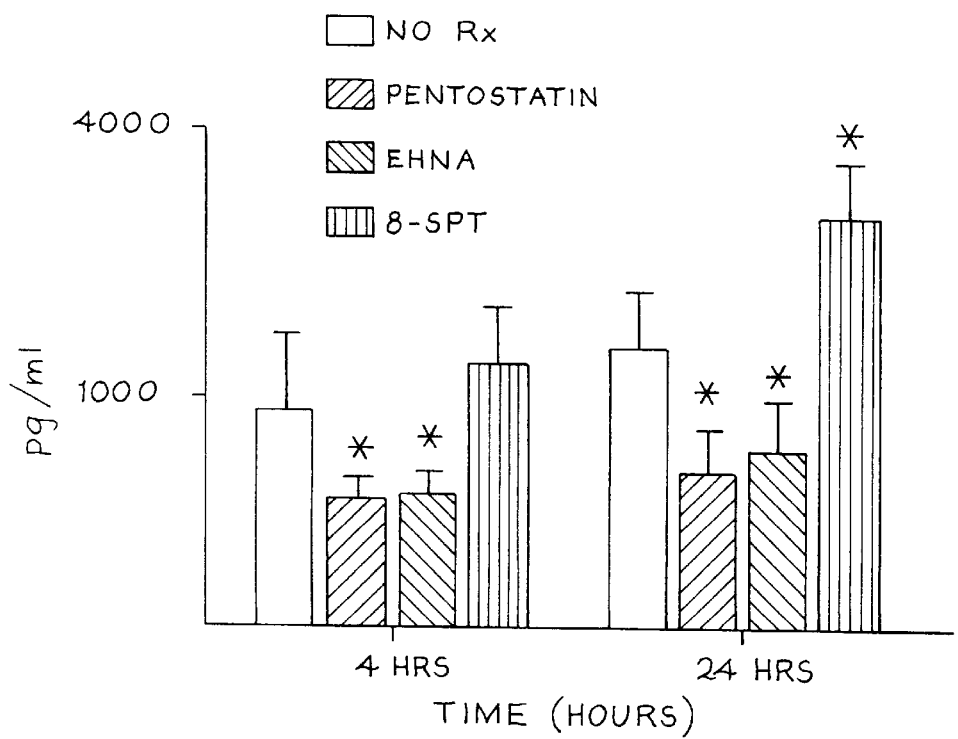
FIG. 4 graphically compares levels of serum tumor necrosis factor-alpha at 4 hours and 24 hours after treatment with either no formulation, pentostatin, EHNA or 8-SPT.
Figure 5:
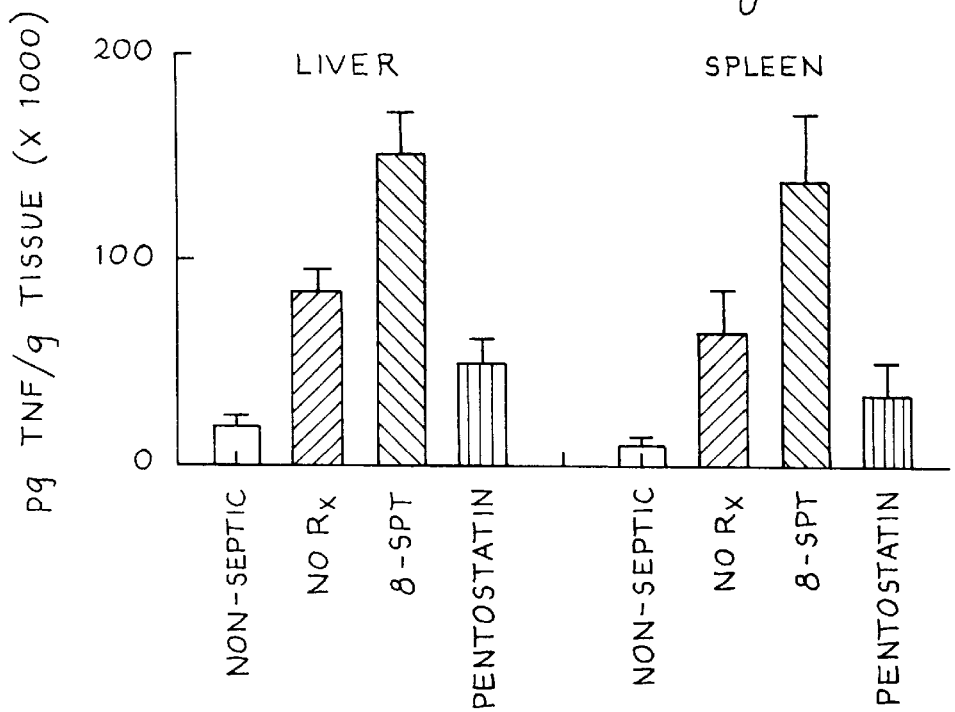
FIG. 5 graphically compares levels of TNF in liver and in spleen from non-septic animals and septic animals treated with no formulation, 8-SPT or pentostatin.

Studies were conducted to determine if manipulation of adenosine-mediated events would result in alterations in the TNF-α response in this model. At the time of sepsis induction, rats were treated in one of four ways. One group received only 0.9% normal saline as a vehicle control (No $R_x$; n=6). A second group were treated with the adenosine deaminase inhibitor, pentostatin (5 mg/kg/12 hours ip; n=5), to prevent enzymatic degradation of endogenous adenosine. The third group received the adenosine deaminase inhibitor, erythro-9-(2-hydroxy-3-nonyl)adenine (EHNA; 1 μmole/kg+1 μmole/kg/hr; iv; n=3). A fourth group received the adenosine receptor antagonist 8-sulfophenyltheophylline (SPT; 400 μg/kg/8 hours; n=5). Results are shown in FIG. 4. In the No $R_x$ septic group, sepsis resulted in elevated serum TNF-α at 4 and 24 hours, similar to that seen in FIG. 2. Inhibition of adenosine deaminase with either pentostatin or EHNA resulted in attenuation of this response at both 4 and 24 hours after sepsis induction. SPT amplified the response at 24 hours, but not at 4 hours. Similar responses were seen in liver and spleen TNF-α concentrations (FIG. 5). The results indicate that preventing endogenous adenosine degradation diminishes the in vivo TNF-α response to sepsis, while blockade of adenosine receptors amplifies this response. These data are consistent with the hypothesis that manipulating endogenous adenosine during sepsis can be used to effectively modulate serum TNF-α concentrations. In neither the adenosine deaminase inhibition nor the 8-SPT groups were blood pressures or heart rates significantly different from saline-treated septic rats. Importantly, chronic adenosine deaminase inhibition did not result in exacerbation of hypotension associated with sepsis. In addition, it is noteworthy that 3 of the 5 saline-treated septic rats survived to day 3, while 4 of the 5 septic rats treated with pentostatin survived to 3 days post-sepsis, and only 2 of the 5 treated with 8-SPT survived. An interpretation of these data suggest that endogenous adenosine plays an important role in sepsis, and that inhibition of adenosine deaminase can exert beneficial effects via modulation of the immune response.

Oxidative Tissue Damage

Figure 6:
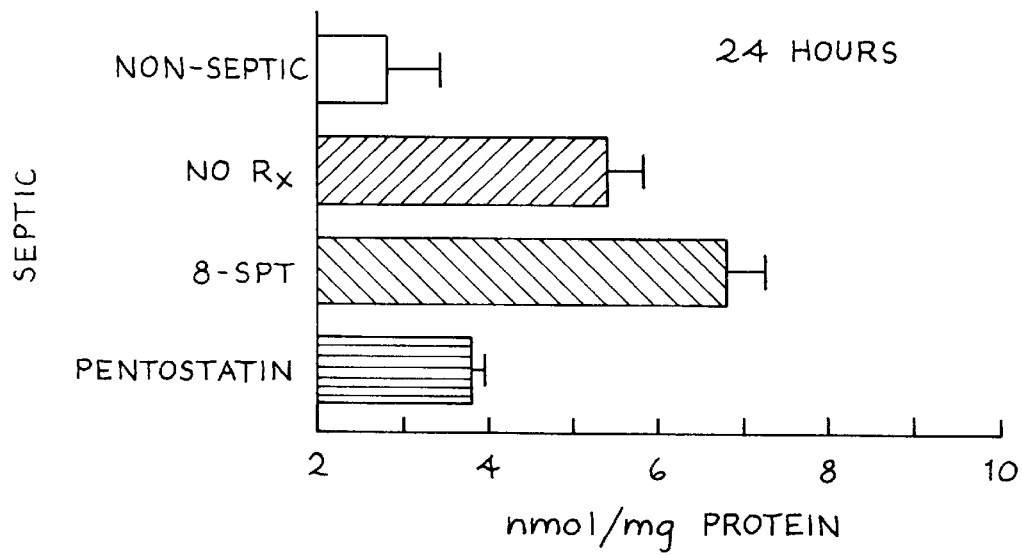
FIG. 6 shows the 24 hour levels of thiobarbituric acid reactive substances from the jejeunum in non-septic animals and in septic animals treated with no formulation, with 8-SPT or with pentostatin.

Concentrations of the products of lipid peroxidation [thiobarbituric acid reactive substances (TBARS)] were measured using the thiobarbituric acid reaction from representative samples of jejunum tissue of septic and control rats at 24 and 72 hours after sepsis induction. Tissue homogenate samples (0.2 ml; 10% w/v) were combined with 0.2 ml 8.1% sodium dodecyl sulfate, 1.5 ml of 20% acetic acid (the solution adjusted to pH 3.5 with NaOH), and 1.5 ml of 0.8% aqueous solution of thiobarbituric acid. Distilled water was added to bring the total volume up to 4 ml, then heated in an oil bath at 950° C. for 60 min. After cooling, 1 ml distilled water and 5 ml n-butanol/pyridine (15:1 v/v) was added. After shaking 30 sec, followed by centrifugation at 4000 rpm for 10 min, absorbance of the organic layer was measured at 532 nM. Data from tissue obtained from non-septic rats, and septic rats treated with saline (No Rx), 8-SPT, or pentostatin are expressed as nmols TBARS per mg protein in FIG. 6 Elevated TBARS were found as early as 24 hours after sepsis induction. Adenosine receptor blockade (8-SPT) resulted in exacerbation of the sepsis-induced elevation in TBARS. Inhibition of adenosine deaminase with pentostatin resulted in diminution of tissue TBARS during sepsis. These data confirm the presence of oxidative damage in this model of sepsis, and the ability to reduce oxidative damage by inhibiting adenosine deaminase. The data demonstrating exacerbation of oxidative damage with adenosine receptor blockade points to the primary role for endogenous adenosine in these responses.

Evidence of Adenosine Involvement in Altered Perfusion in Sepsis/SIRS

Systemic vascular responses were examined 24 hours after induction of sepsis in the presence or absence of adenosine receptor blockade in septic and non-septic rats using radiolabelled microspheres. For these experiments, the surgical procedure involving vascular access was modified to include a catheter in the left ventricle of the heart (via the carotid artery), and a catheter in the tail artery (Intramedic PE-50, Baxter) to permit reference blood withdrawal and blood pressure monitoring. Regional blood flows were determined using radiolabelled microspheres. The microspheres (15 μM New England Nuclear, Boston), labeled with one of four isotopes ($^{46}$Sc, $^{85}$Sr, $^{95}$Nb, $^{141}$Ce), were mixed in 0.9% normal saline with 0.01% Tween-80 added to prevent aggregation. The microspheres were adjusted to provide a minimum of 400 microspheres per tissue sample, and represented approximately 100,000–250,000 spheres per injection. The specific isotopes and their order of injection were randomized in each experiment, with each injection representing a volume of 0.4 ml/injectate. The microspheres were sonicated for a minimum of 30 minutes, and vortexed vigorously for at least 30 seconds prior to injection. A reference withdrawal sample was taken at 0.33 ml/min from the tail artery catheter using a mechanical pump (Harvard Model 22). The reference withdrawal was started 10 seconds prior to injecting the isotopes, and continued for 150 seconds. The microspheres were injected into the LV (to ensure adequate mixing) at a constant rate over 15 seconds, and the catheter slowly flushed with 0.9% NSal. Right and left renal and testicular blood flows were compared in each animal to confirm uniform distribution of the microspheres. Tissues collected at necropsy for this study included the hepatosplanchnic organs (liver, spleen, pancreas, colon, stomach, cecum, and small intestine), epididymal adipose tissue, skeletal muscle (from the rectus and hind limb), testes, and kidneys. Wet weights were obtained and all tissues were counted in a gamma spectrophotometer (Beckman 9000). Gamma activity in the injectate vials was counted prior to the experiments. Actual injected amounts for each isotope were calculated by subtracting any isotope counts remaining in the vials, syringes, and catheters used for injection. Cardiac output (CO) was determined by dividing the total injectate counts for any given isotope by the counts in the reference sample and multiplying by the fixed withdrawal rate of the reference sample. The results for cardiac output are expressed as ml/min. Tissue counts attributed to each isotope were determined after subtracting the overlap of energy spectra from higher energy isotopes (Compton back-scatter). Individual tissue blood flows were determined by dividing the counts obtained in the tissue by the reference withdrawal counts and multiplying by the reference withdrawal rate. Tissue blood flows were then normalized to wet weight was calculated by adding the individual tissue blood flows of the stomach, small intestine, cecum, colon, pancreas, hepatic artery and spleen, and dividing by the liver weight. Regional tissue vascular resistances were calculated from regional blood flows and arterial blood pressure, according to the equation:

Regional vascular resistance=mean arterial blood pressure/regional blood flow.

Figure 7:
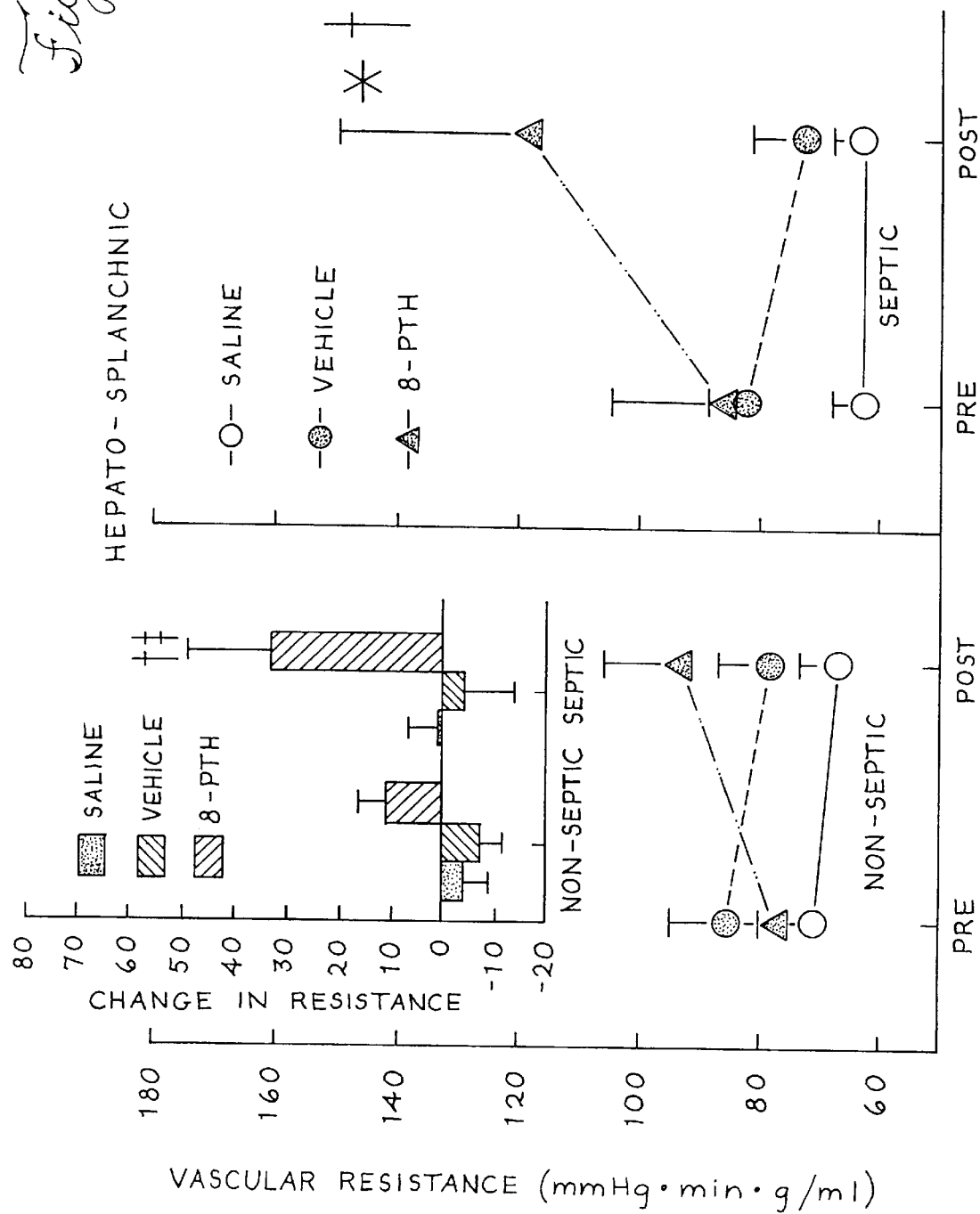
FIG. 7 graphically illustrates vascular resistance and chenge in resistance in hepato-splanchinic systems of septic and non-septic animals treated with saline, a vehicle, or 8-PTH.
Figure 8:
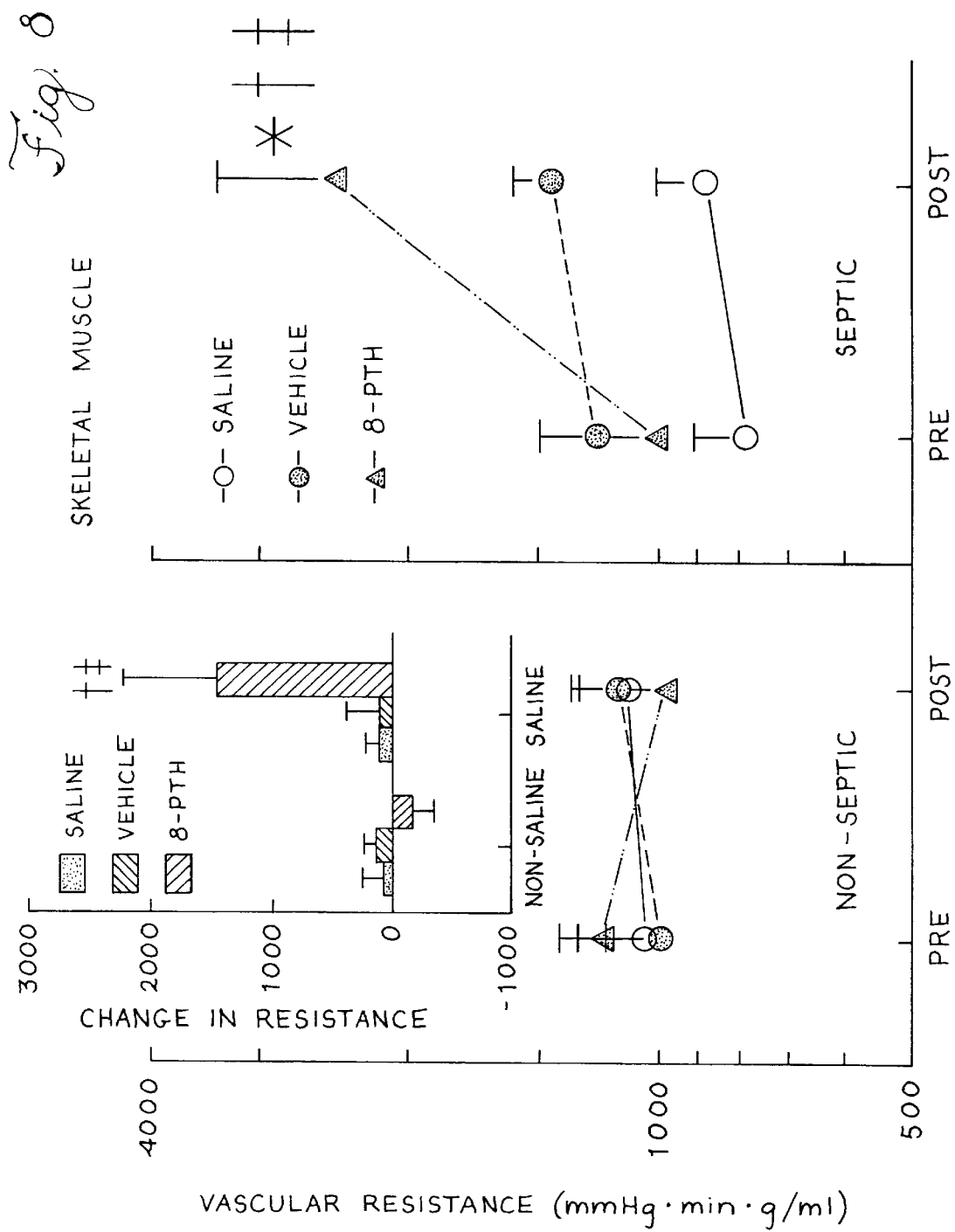
FIG. 8 graphically illustrates vascular resistance and change in resistance in skeletal muscles of non-septic and septic animals treated with saline, a vehicle, and 8-PTH.
Figure 9:
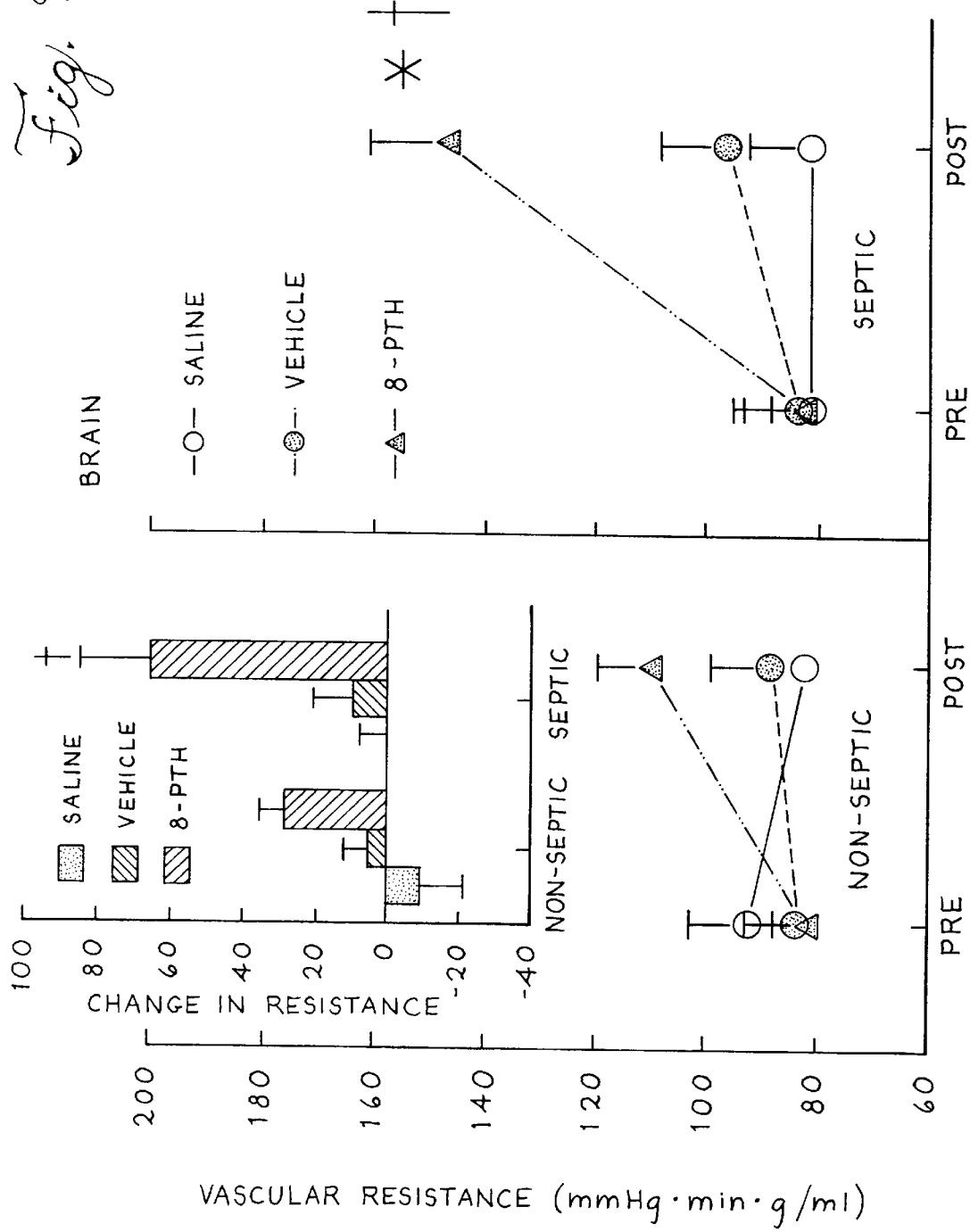
FIG. 9 graphically illustrates vascular resistance and change in resistance in brains of non-septic and septic animals treated with saline, a vehicle, or 8-PTH.
Figure 10A:
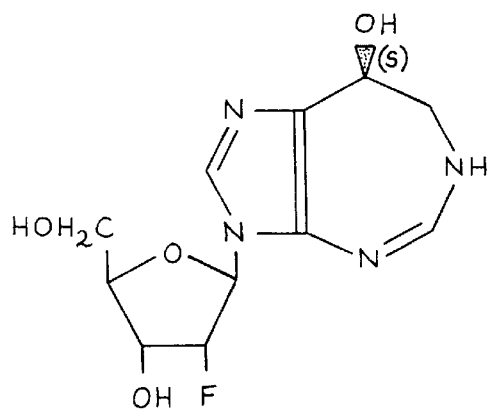
FIG. 10A shows 2'-deoxy-2'-fluorocoformycin.
Figure 10B:
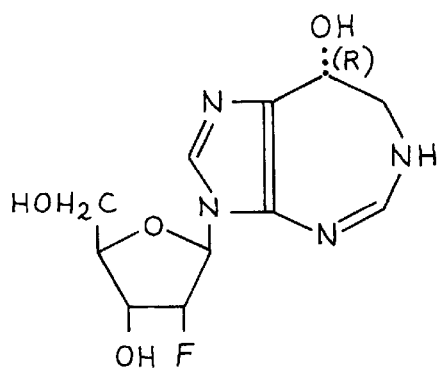
FIG. 10B shows 2'-deoxy-8-epi-2'-fluorocoformycin. Both of these compounds have high enzyme-inhibitory activities against adenosine deaminase.
Figure 11:
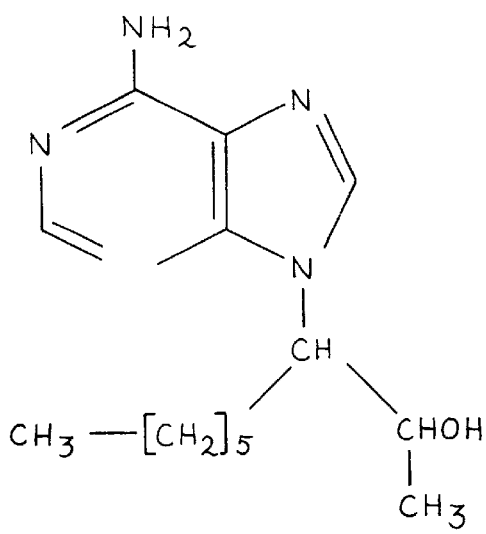
FIG. 11 shows erythrohydroxynonyl adenine (EHNA).
Figure 12:
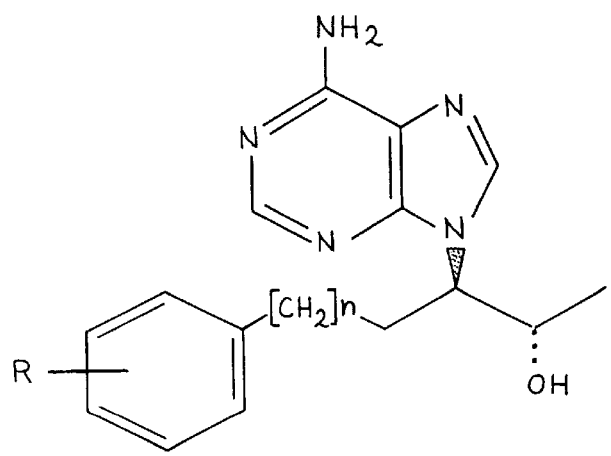
FIG. 12 shows a general chemical structure of (2S,3R)-3(6-aminopurin-9yl)arylakan-2-ols (also called 9-aralkyladenines, or ARADS).

Twenty-four hours after sepsis induction, hepato-splanchnic, skeletal muscle, and adipose blood flows were significantly higher than in non-septic rats. The administration of the non-selective adenosine antagonist, 8-phenyltheophylline (8-PTH), caused increases in total hepato-splanchnic (FIG. 7), skeletal muscle (FIG. 8), and brain vascular resistances (FIG. 9) in septic rats, but not in non-septic rats. The use of 8-PTH required a special vehicle (30 mM NaOH, 8.5% ethyl alcohol, and 0.1 M NaCl.), which had no effect in either septic or non-septic rats. The use of 8-SPT had similar effects as 8-PTH, with the exception of changes in cerebral vascular resistance, owing to the inability of 8-SPT to cross the blood-brain barrier. These data demonstrate that endogenous adenosine is important in maintaining lower resting vascular tone in skeletal muscle and hepato-splanchnic circulations during sepsis. Based on the similar ability of 8-SPT to block the salutary effects of adenosine on immune and oxyradical-mediated responses during sepsis, and the beneficial effects of inhibiting adenosine deaminase relative to these responses, it is reasonable to speculate that inhibition of adenosine deaminase would result in greater reductions in hepato-splanchnic, muscle, and cerebral vascular resistances during sepsis, resulting in elevated blood flows to these regions.

Reduction in Capillary leakage

Examination of untreated septic rats, and septic rats treated with the adenosine deaminase inhibitor, pentostatin, or the adenosine receptor antagonist, 8-SPT, revealed the following findings. The peritoneal cavity of the untreated septic rats contained between 2–3 ml of sero-sanguinous fluid. This volume was increased to 3–5 ml in septic rats treated with 8-SPT. In pentostatin-treated septic rats, there was 0–1 ml of serous fluid (free of red cells). Untreated septic rats also demonstrated evidence of small bowel hemorrhage, and the lumen of sporadic, 3–4 cm segments of the small bowel were distended with fluid. In septic rats treated with 8-SPT, small bowel hemorrhaging was evident, and the entire small bowel was dusky in appearance. The entire length of the small bowel, and much of the cecum and colon, was distended with fluid, and the animals experienced bloody diarrhea. In septic rats treated with pentostatin, there was little to no evidence of small bowel hemorrhage, and the lumen contents appeared normal, including formed stool in the colon. This evidence is consistent with problems associated with capillary leakage and fluid exudation during untreated sepsis, exacerbation of capillary leakage upon treatment with 8-SPT, and amelioration of capillary leakage upon treatment with pentostatin.

Formulations

For the purposes of this invention, the compounds of the invention may be administered by a variety of means including orally, parenterally, by inhalation spray, sublingually, topically, or rectally in formulations containing conventional non-toxic pharmaceutically acceptable carriers, adjuvants and vehicles. The term parenteral as used herein includes sub-cutaneous, intravenous, intramuscular, and intraarterial injections with a variety of infusion techniques. Intraarterial and intravenous injection as used herein includes administration through catheters. Preferred for certain indications are methods of administration which allow rapid access to the tissue or organ being treated, such as intravenous injections. When an organ outside a body is being treated, perfusion is preferred.

Pharmaceutical compositions containing the active ingredient may be in any form suitable for the intended method of administration.

The pharmaceutical compositions of the invention may be in the form of a sterile injectable preparation, such as a sterile injectable aqueous or oleaginous suspension. This suspension may be formulated according to the known art.

The amount of active ingredient that may be combined with the carrier material to produce a single dosage form will vary depending upon the host treated, the particular mode of administration, and the active ingredient used.

It will be understood that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Examples of use of the method of the invention includes the following. It will be understood that these examples are exemplary and that the method of the invention is not limited solely to these examples.

The method may be used in septic patients in whom oral administration is counter-indicated, as is well understood by those skilled in the art. The compound would be given as a sterile injectable preparation intravenously, for example, as a suspension of solution formulated according to the known art suitable for the active ingredient.

MATERIALS AND METHODS

ENHA (FIG. 11)

Erythrohydroxynonyl adenine (ENHA) was discovered by Schaeffer et al. (1974). A difference between EHNA and pentostatin is the potency of inhibition of the enzyme. EHNA has a $K_i$ value of $10^{-9}$ M which makes it one thousand times less active than pentostatin. Another major difference between the two drugs is their duration of inhibition of ADA. Unlike pentostatin, inhibition with EHNA is reversible with a half life of half an hour. This difference is based on the fact that the EHNA is apparently metabolized by liver enzymes to oxidized (hydrolyzed) metabolites which are excreted in the urine (McConnell et al.).

ARADS (FIG. 12)

ARADS are (2S,3R)-3(6-Aminopurin-9-yl)arylakan-2-ols (also called 9-aralkyladenines), where the alkyl group is composed of 4–8 carbon atoms having a hydroxyl group at carbon#2 with (S) chirality and an adenine ring attached through the nitrogen at position#9 to carbon#3 with (R) chirality. The terminal carbon of this alkyl chain is attached to an aromatic ring (phenyl, napththyl, thienyl, furanyl, etc.) which ring can be substituted with alkyl, halide, hydroxy, carboxylic acid, ester, ether, azide, amine, and other moieties to make useful analogs. These are a novel class of adenine derivatives which have been shown to inhibit the enzyme adenosine deaminase at therapeutically useful levels. The relevant inhibitory constant ($K_i$) values are in the range of $10^{-7}$–$10^{-10}$ M. These compounds with potencies in this range can reversibly inhibit ADA in an effective manner, without permanently deactivating the enzyme. ADA inhibitors that have similar biological profiles have been shown to be of therapeutic value when used to protect heart muscle against ishemic damage.

Model of SIRS/sepsis

All of the studies on the effects of adenosine deaminase inhibitors were performed in a model of chronic peritoneal sepsis developed by the inventors that results in systemic inflammatory response syndrome (SIRS). Sepsis was induced under pentobarbital anesthesia (50 mg/kg) in each rat by intraperitoneal (ip) injection of 200 mg/kg rat cecal contents mixed as a slurry in 5% dextrose in water (D5W). The cecal slurry was prepared from fresh cecal contents of a donor rat and was used within two hour of collection to induce sepsis. Non-septic controls received an equivalent volume ip injection of D5W. Polyethylene catheters (Intramedic PE-50, Baxter) were inserted into the right internal jugular vein and right carotid artery. The jugular catheter was used for venous access (drug infusions; volume replacement, etc). The carotid catheter was used to obtain arterial blood samples, and to monitor arterial blood pressure and heart rate. The catheters were secured in their respective vessels, tunneled subcutaneously to exit in the interscapular region, and filled with heparinized saline (50 units/ml 0.9% normal saline). Incisions were closed in layers using 3-0 silk. Rats were allowed to recover from anesthetic and provided food and water ad libitum.

TNF-α is Modulated by Adenosine Deaminase Inhibition

Serum and tissue tumor necrosis factor-alpha (TNF-α) concentrations were determined by enzyme-linked immunosorbant assay. Samples of serum, liver, and spleen were collected, rapidly weighed, and frozen in liquid nitrogen. On the day of assay, tissues are added to labeled tubes containing lysis buffer (volume=10 ml/gram wt. with 1:10 dilution) and kept on ice. The lysis buffer is 20 mM Tris (pH 7.4) containing 170 l/ml phenylmethylsulfonylflouride (PMSF), 0.5 g/ml leupeptin, 0.7 g/ml pepstatin, and 2.0 g/ml aprotinin to inhibit proteases. Samples were immediately homogenized using five 3 sec bursts, washing grinding pistol (3×) between samples with phosphate buffered saline. Samples are then centrifuged for 20 min at 2200 RPM, 4° C. The supernatant was removed and used for TNF-α measurements. Briefly, each microplate well contained 50 μl of assay diluent. To each well, 50 μl of standard, control, or serum/homogenate supernatant sample were added and mixed on an orbital plate shaker. Plates were incubated at room temperature for 2 hours. Each well was then aspirated and washed with wash buffer 4 times. After final aspiration of wash buffer, 100 μl of rat TNF-α conjugate was added to each well. Wells were then covered and incubated for 2 hours at room temperature. At the end of the incubation, the aspiration/wash procedure was repeated 4 times, after which 100 μl of stabilized chromogen solution was added to each well. Next, plates were incubated for 45 minutes at room temperature in a dark area. After this final incubation period, 100 μl stopping solution was added to each well. Optical density of each well at 450 nM was determined within 30 minutes using a Biotek Instruments EL312e microtiter plate reader. Concentrations of TNF-α were calculated from the standard curves.

EXAMPLES

The following examples illustrate some of the embodiments of the invention:

Example 1

Use of Pentostatin, an Adenosine Deaminase Inhibitor, to Attenuate Sepsis in Rats Pentostatin inhibits adenosine deaminase during sepsis in rats. Rats weighing 325–400 g were anesthetized with an intraperitoneal (ip) injection of pentobarbital sodium (Abbott, 50 mg/kg). Polyethylene catheters (Intramedic PE-50, Baxter) were inserted into the right internal jugular vein and the right carotid artery. The jugular catheter was used for venous access (drug infusions, volume repletion, and so forth). The carotid catheter was used to obtain arterial blood samples, and to monitor arterial blood pressure and heart rate. The catheters were secured in their respective vessels, tunneled subcutaneously to exit in the interscapular region, and filled with heparinized saline (50 units/ml, 0.9% normal saline). Incisions were closed in layers using 3-0 silk.

At the time of sepsis induction, rats were treated in one of three ways. One group received only 0.9% normal saline as a vehicle control (VEH, n=6, where n is the number of rats). A second group was treated with the adenosine deaminase inhibitor, pentostatin (5 mg/kg/12h; n=5). A third group received the adenosine receptor antagonist, 8-sulfophenyltheo-phylline (SPT; 400μg/kg/8h; n=5). Serum TNF-α (pg/ml) was determined at 4 and 24 hours after sepsis induction by ELISA. In the VEH group, sepsis resulted in elevated TNF-α at 4 and 24 hours. In the treated group, Pentostatin resulted in attenuation of this response at both 4 and 24 hours after sepsis induction. SPT amplified the response at 24 hours, but not at 4 hours. The results of this example indicate that preventing endogenous adenosine degradation with pentostatin diminishes the in vivo TNF-α response to sepsis, while blockade of adenosine receptors amplifies this response. These data are consistent with the hypothesis that manipulating endogenous adenosine during sepsis can be used to effectively modulate serum TNF-α concentrations. In neither the groups treated with pentostatin nor the groups treated with 8-SPT were blood pressures or heart rates significantly different from saline-treated septic rats. Importantly, chronic adenosine deaminase inhibition did not result in exacerbation of hypotension associated with sepsis. In addition, 3 of the 6 saline-treated septic rats survived to day 3, while 4 of 5 septic rats treated with pentostatin survived to 3 days post-sepsis, and only 1 of 5 treated with 8-SPT survived to 3 days. The conclusion is that endogenous adenosine plays an important and beneficial role in attenuating sepsis.

Example 2

Manipulation of Endogenous Adenosine Modulates Serum Tumor Necrosis Factor-Alpha (TNF-α) During Sepsis in Rats Endogenous adenosine (ADO) is known to modulate macrophage TNF-α production in vitro. During sepsis, endogenous ADO plays a significant role in determining resting vascular resistance in selected regions in vivo. Manipulation of endogenous ADO during sepsis modulates serum TNF-α concentration in vivo, as follows:

Male SD rats (350–400 g) were made septic by IP introduction of a 200 mg/kg cecal slurry. At the time of sepsis induction rats were treated with the ADO deaminase inhibitor pentostatin (PNT; n=5), the ADO receptor antagonist 8-sulfo-phenyltheophylline (SPT; n=5), or vehicle (VEH; 0.9% NaCl; n=6). TNF-α (pg/ml) was determined at 4 and 24 hours after sepsis induction by ELISA. Significant differences from the VEH treated group over time (p≦0.05) were determined by 2-way ANOVA followed by the Tukey test.

In the VEH group, sepsis resulted in elevated TNF-α, at 4 (934±453) and 24 hours (1287±437). PNT resulted in attenuation of this response at both 4 and 24 hours after sepsis induction (592±62 and 671±175, respectively). SPT amplified the response at 24 hours (2479±875), but not at 4 hours (1167±428).

The results indicate that preventing endogenous ADO degradation with PNT diminishes the in vivo TNF-α response to sepsis, while blockade of ADO receptors amplifies this response. These data suggest that manipulating endogenous adenosine during sepsis can be used to effectively modulate rather than completely ablate the TNF-α response to sepsis. Modification of adenosine pathways is a useful tool in the management of sepsis.

DOCUMENTS CITED

Abd-Elfattah, A. S., M. E. Jessen, S. A. Hanan, G. Tuchy, A. S. Wechsler, *Circ.* 82 (5 Suppl), IV341 (1990).

Abraham, E. et al., *Lancet* 351, 929 (1998).

Adamik, B., M. Zimecki, A. Waszczyk, and A. Kübler, *Arch. Immunol. Ther. Exp.* (Warsz) 45, 169 (1997).

Amiot, F., C. Fitting, K. J. Tracey, J. M. Cavaillon, F. Dautry, *Mol. Med.* 3, 864 (1997).

Arvidsson, S., K. Fält, U. Haglund, *Acta Chir. Scand.* 156, 215 (1990).

Barankiewicz, J., A. Cohen, *Eur. J. Immunol.* 15, 627 (1989).

Becker, B. F., E. Gerlach, Topics and Perspectives in Adenosine Research, E. Gerlach and B. F. Becker, Eds. (Springer-Verlag, Berlin; Heidelberg, 1987), p. 209.

Belardinelli et al., *Prog. in Cardiovasc. Diseases*, 1989, 32:73–97.

Broner, C. W. et al., *Circ.Shock* 29, 77 (1989).

Casey, L. C., R. A. Balk, R. C. Bone, *Annals of Int. Med.* 119, 771 (1993).

Castillo, M., L. H. Toledo-Pereyra, R. Gutierrez, D. Prough, E. Shapiro, *Amer. Surg.* 57, 313 (1991).

Cohen, J., J. Carlet, Crit. Care Med. 24, 1431 (1996).

Cronstein, B. N., et al., *J. Immnunol.* 148, 2201 (1992).

Cronstein, B. N., D. Naime, G. Firestein, Arthritis and Rheumatism 38, 1040 (1995).

Cronstein et al., *J Clin. Invest.*, 1986, 78:760–770.

Eigler, A., et al., *Scand.J.Immunol.* 45, 132 (1997).

Firestein et al., *J.Immunol.*; 152, 5853–5859.

Haskó, G. et al., *J.Immunol.* 157, 4634 (1996). Itoh, K., T. Majima, K. Edo, M. Mizugaki, N. Ishida, Tohoku J.Exp.Med. 157, 205 (1989).

Kato, T., et al., Antimicrob. Agents Chemother. 39, 1336 (1995).

Leff, J. A., et al., *Lancet* 341, 777 (1993).

LeMoine, O., et al, *J. Immunol.* 156, 4408 (1996).

McConnell et al., *CBA Mice Biochem. Pharmacol.*, 1983.

Meduri, G. U., et al., *Chest* 107, 1062 (1995).

Morgan, R. A., et al., *Circ. Shock* 25, 319 (1988).

Moser et al., Am. *J. Physiol.*, 1989, 256: C799–C806.

Motew, S. J., M. G. Mourelatos, R. N. Miller, J. L. Ferguson, W. R. Law, *Shock* 7, 439 (1997).

Motew, S. J., et al., *J Surg. Res.* 80, 326 (1998).

Parmely et al., FASEB *Journal*, 1991, 5: A 1602.

Peralta, J. G., et al., *Circ. Shock* 39, 153 (1993).

Riches, D. W. H., J. L. Watkins, P. M. Hensen, D. R. Stanworth, *J. Leukocyte Biol.* 37, 545 (1985).

Richter, J., *J. Leukocyte Biol.* 51, 270 (1992).

Ritchie, P. K., et al., *Cytokine* 9, 187 (1997).

Schaeffer, H. J. and C. F. Schwender, *J. Med. Chem.*, 17:68, 1974.

Schiller, H. J., P. M. Reilly, G. B. Bulkley, *Crit. Care Med.* 21, S92 (1993).

Schrader, in *Regulatory Function of Adenosine*, Beme et al. eds., pp. 133–156, 1983.

Schrier et al., *J. Immunol.*, 1990, 145:1874–1879.

Spitzer, J. A., P. Zhang, A. A. Mayer, *J. Leukocyte Biol.* (1994). 56: 166–173.

U.S. Pat. No. 5,646,128; Firestein et al.; Jul. 8, 1997: Method for Treating Adenosine Kinase Related Conditions.

U.S. Pat. No. 5,643,035; French et al.; Oct. 31, 1995: Process for Purifying Pentostatin.

Walley, K. R., N. W. Lukacs, T. J. Standiford, R. M. Strieter, S. L. Kunkel, *Infect. Immun.* 64, 4733 (1996).

Xu, D., et al., *J. Trauma* 34, 676 (1993).

Zager, R. A., *Circ. Res.* 68, 185 (1991).

What is claimed is:

1. A method for treating systemic inflammatory response syndrome (SIRS) in a mammal in need of the treatment, said method comprising administering to said person an amount of an inhibitor of adenosine deaminase effective to ameliorate symptoms of the syndrome.

2. The method of claim 1, wherein the symptoms of the syndrome is an inflammatory response and to ameliorate the symptom is to decrease it.

3. The method of claim 1, wherein the symptom is sepsis and it is reduced.

4. The method of claim 1, wherein the inhibitor is pentostatin.

5. The method of claim 1, wherein the inhibitor is EHNA.

6. The method of claim 1, where the inhibitor is ARADS.

7. A method of affecting the factors involved in the systemic inflammatory response syndrome in a mammal, said method comprising administering to the mammal an amount of an inhibitor of adenosine deaminase effective to affect the levels of the factors.

8. The method of claim 7, wherein the factor is TNF– and wherein this factor is affected by reducing levels below those in comparable mammals that are septic and had not been treated with an adenosine deaminase inhibitor.

9. The method of claim 7, wherein the factor is thiobiarituric acid reactive substance (TBARS) and the factor is affected by diminution of the level of TBARS.

10. The method of claim 7, wherein the factor is systemic vascular responses after induction of sepsis, and the factor is affected by increased blood flow.

11. A method for treating tissues affected by burns, said method comprising increasing local concentration of adenosine in the tissues by contacting them with an effective dose of adenosine deaminase inhibitors.

\* \* \* \* \*